(12) United States Patent
Watkins et al.

(10) Patent No.: US 12,415,228 B2
(45) Date of Patent: Sep. 16, 2025

(54) INTEGRATED VIZOR CONTROLS FOR A HELMET AND CORRESPONDING HELMETS

(71) Applicant: WALTER SURFACE TECHNOLOGIES INC., Pointe-Claire (CA)

(72) Inventors: James Watkins, East Taunton, MA (US); Jason Pereira, Taunton, MA (US)

(73) Assignee: WALTER SURFACE TECHNOLOGIES INC., Windsor, CT (US)

( * ) Notice: Subject to any disclaimer, the term of this patent is extended or adjusted under 35 U.S.C. 154(b) by 0 days.

(21) Appl. No.: 18/291,805

(22) PCT Filed: Jul. 29, 2022

(86) PCT No.: PCT/US2022/074310
§ 371 (c)(1),
(2) Date: Jan. 24, 2024

(87) PCT Pub. No.: WO2023/010116
PCT Pub. Date: Feb. 2, 2023

(65) Prior Publication Data
US 2024/0375204 A1 Nov. 14, 2024

Related U.S. Application Data

(60) Provisional application No. 63/227,436, filed on Jul. 30, 2021.

(51) Int. Cl.
*A42B 3/22* (2006.01)
*B23K 9/32* (2006.01)

(52) U.S. Cl.
CPC .............. *B23K 9/322* (2013.01); *A42B 3/225* (2013.01)

(58) Field of Classification Search
CPC .................................. A42B 3/22; B23K 9/322
See application file for complete search history.

(56) References Cited

U.S. PATENT DOCUMENTS 12,108,826 B2 * 10/2024 Huh ...................... A42B 3/225
2013/0340141 A1 12/2013 Huh
(Continued)

FOREIGN PATENT DOCUMENTS

WO 2019111213 A1 6/2019

OTHER PUBLICATIONS

International Search Report and Written Opinion issued in application No. PCT/US22/74310.

*Primary Examiner* — Gloria M Hale
(74) *Attorney, Agent, or Firm* — McClure, Qualey & Rodack, LLP

(57) ABSTRACT

A protective helmet having a shell which at least partially delimits a head-receiving cavity is provided. The helmet includes an electronic assembly mounted to the helmet shell and having at least one controllable setting. A face-protecting member is mounted to the helmet shell; wherein the face-protecting member comprises at least one panel tab. The panel tab is selectively depressible to cooperate with an actuator mounted to or formed integral with the helmet shell and operatively coupled to the electronic assembly to adjust the at least one controllable setting upon depression of the at least one panel tab.

20 Claims, 14 Drawing Sheets

(56) References Cited

U.S. PATENT DOCUMENTS

| | | |
|---|---|---|
| 2014/0013479 A1 | 1/2014 | Magnusson |
| 2014/0259252 A1 | 9/2014 | Seo |
| 2016/0081856 A1 | 3/2016 | Hofer-Kraner |
| 2017/0143547 A1* | 5/2017 | Watkins ................ A42B 3/225 |
| 2017/0173720 A1* | 6/2017 | Sumner ................ B23K 9/0953 |
| 2018/0071854 A1* | 3/2018 | Matthews .............. H04N 7/183 |
| 2018/0184746 A1* | 7/2018 | Plebani ................ A42B 3/225 |
| 2019/0216649 A1 | 7/2019 | Watkins |
| 2019/0274885 A1* | 9/2019 | Huh ..................... A42B 3/225 |
| 2020/0085132 A1* | 3/2020 | Segura ................ A42B 3/225 |
| 2023/0180877 A1* | 6/2023 | Brouwer ............... A42B 3/06 |
| | | 2/419 |
| 2024/0375204 A1* | 11/2024 | Watkins ................ A42B 3/225 |

* cited by examiner

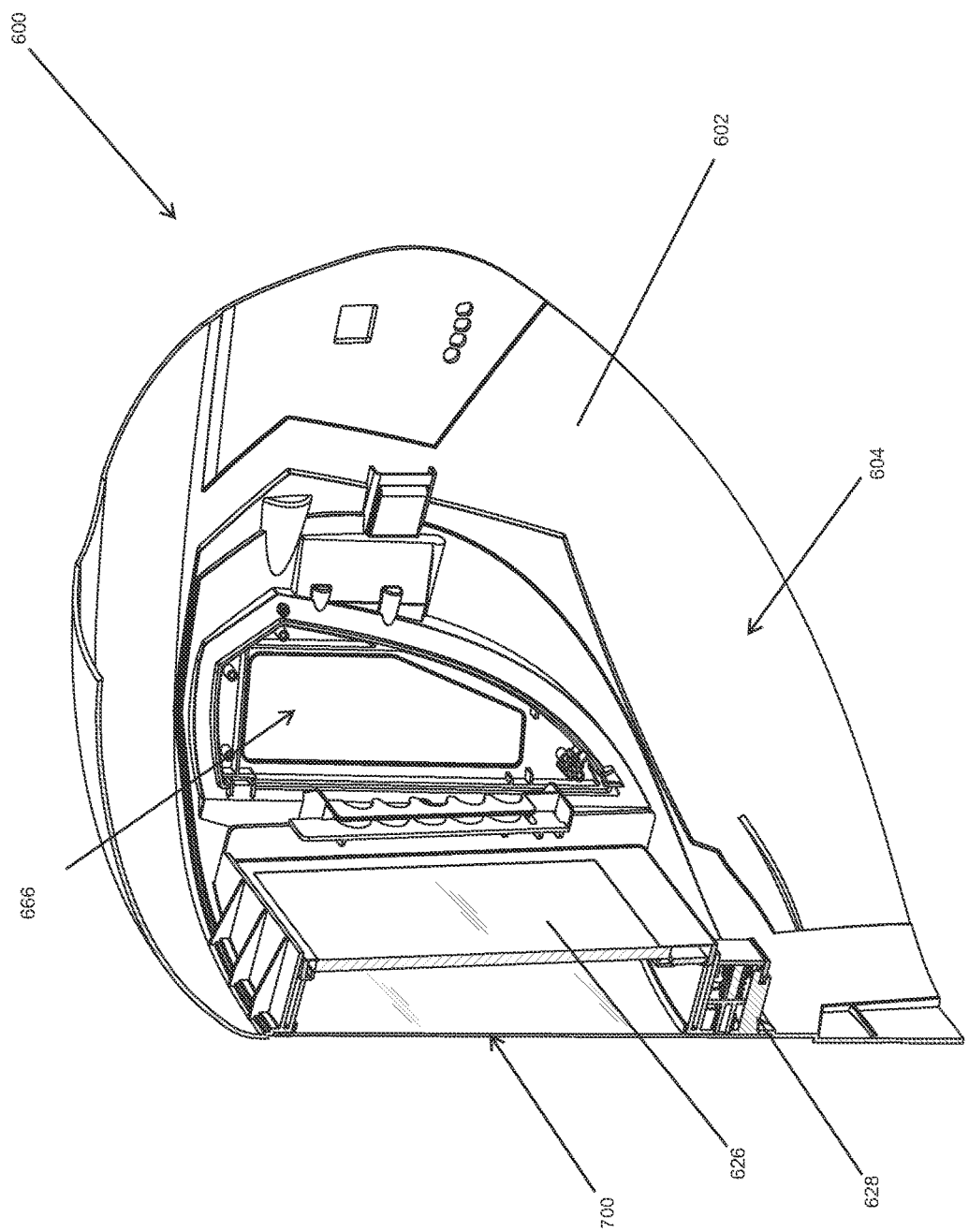

INTEGRATED VIZOR CONTROLS FOR A HELMET AND CORRESPONDING HELMETS

PRIOR APPLICATION

The present application claims priority from U.S. provisional patent application No. 63/227,436, filed on Jul. 30, 2021, and entitled "INTEGRATED VIZOR CONTROLS FOR A HELMET AND CORRESPONDING HELMETS", the disclosure of which being hereby incorporated by reference in its entirety.

TECHNICAL FIELD

The present disclosure relates generally to safety equipment and, more particularly, to welding helmets.

BACKGROUND

Welding helmets are typically used in the mechanical and industrial fields to protect welders from harmful irradiation emitted from welding arcs and from splashes, sparks and particles that may be ejected from a welding area. Some welding helmets are furnished with an auto-darkening welding filter which automatically changes from a light-state to a dark-state in response to incident light generated by the welding arc. In order to protect the auto-darkening welding filter, welding helmets might further comprise a face-protecting member (or screen-protecting member) mounted to a helmet shell of the welding helmet. The settings of the filter may be manually modified by manipulating buttons mounted to or formed integral with the helmet shell, but the face-protecting member needs to be configured in an open position for the user to reach these buttons, leaving the welding filter unprotected. Moreover, the buttons may be accidentally actuated, break or become faulty due to buildup of dirt.

In view of the above, there is a need for a welding helmet which would be able to overcome or at least minimize some of the above-discussed prior art concerns.

BRIEF SUMMARY

It is therefore an aim of the present invention to address the above-mentioned issues.

According to a general aspect, there is provided a protective helmet, comprising a helmet shell at least partially delimiting a head-receiving cavity; an electronic assembly having at least one controllable setting; and a face-protecting member mountable to the helmet shell to configure the protective helmet into a closed configuration; wherein the face-protecting member comprises at least one panel tab selectively depressible to cooperate with an actuator mounted to or formed integral with the helmet shell and operatively coupled to the electronic assembly to adjust said at least one controllable setting upon depression of said at least one panel tab.

According to another general aspect, there is provided a protective helmet, comprising a helmet shell at least partially delimiting a head-receiving cavity; an electronic assembly mounted to the helmet shell and having at least one controllable setting; a face-protecting member mounted to the helmet shell; wherein the face-protecting member comprises at least one panel tab selectively depressible to cooperate with an actuator mounted to or formed integral with the helmet shell and operatively coupled to the electronic assembly to adjust said at least one controllable setting upon depression of said at least one panel tab.

According to another aspect, there is provided a welding helmet, comprising a helmet shell at least partially delimiting a head-receiving cavity, said head-receiving cavity forming a see-through opening in the helmet shell; a welding filter mounted to the helmet shell and covering at least partially the see-through opening, said welding filter having at least one controllable setting; an electronic control system configured to allow adjustment of said at least one controllable setting of the welding filter; a visor mountable to the helmet shell to configure the welding helmet into a welding-protecting configuration, the visor comprising at least one depressible visor button formed integrally with the visor; and at least one filter actuator mounted to or formed integral with one of the helmet shell and the welding filter and operatively coupled to the electronic control system; wherein the at least one depressible visor button is configured to cooperate with the at least one filter actuator upon being pressed, allowing a user to adjust said at least one controllable setting of the welding filter.

According to another general aspect, there is provided a welding helmet, comprising a helmet shell at least partially delimiting a head-receiving cavity, said head-receiving cavity forming a see-through opening in the helmet shell; a welding filter mounted to the helmet shell and covering at least partially the see-through opening, said welding filter having at least one controllable setting; an electronic control system configured to allow adjustment of said at least one controllable setting of the welding filter; a visor mounted to the helmet shell and comprising at least one depressible visor button formed integrally with the visor; at least one filter actuator mounted to or formed integral with the helmet shell and operatively coupled to the electronic control system; wherein the at least one depressible visor button is configured to cooperate with the at least one filter actuator upon being pressed, allowing a user to adjust said at least one controllable setting of the welding filter.

According to yet another aspect, there is provided a welding helmet, comprising a helmet shell; a visor having at least one integrated depressible visor panel tab formed by cutting a pattern into the visor; an electronic assembly secured to the helmet shell, the electronic assembly having at least one controllable setting; and at least one filter actuator formed integral with or mounted to at least one of the helmet shell and the electronic assembly and operatively coupled to an electronic control system of the electronic assembly to control said at least one controllable setting upon actuation thereof; wherein said at least one integrated depressible visor panel tab at least partially covers said at least one filter actuator to adjust said at least one controllable setting upon depression of said at least one integrated depressible visor panel tab.

According to yet another aspect, there is provided a welding helmet, comprising a helmet shell; a visor having at least one integrated depressible visor panel tab formed by cutting a pattern into the visor a button assembly mounted on the helmet shell, the button assembly comprising an actuator panel comprising at least one filter actuator and a button panel having at least one button, the at least one button being operably coupled to the at least one filter actuator; and an electronic assembly secured to the helmet shell, the electronic assembly having at least one controllable setting, the electronic assembly being operatively coupled to the at least one filter actuator to control said at least one controllable setting upon actuation thereof; wherein said at least one integrated depressible visor panel tab at least partially covers said at least one filter actuator and said at least one button to adjust said at least one controllable setting upon depression of said at least one integrated depressible visor panel tab.

According to another general aspect, there is provided a welding helmet, comprising a visor having at least one integrated depressible visor panel tab formed by cutting a pattern into the visor; a helmet shell; an electronic control system secured to the helmet shell, the electronic control system having at least one controllable setting; at least one screen actuator formed integral with or mounted to the helmet shell and operatively coupled to the electronic control system to control said at least one controllable setting upon actuation thereof; wherein said at least one integrated depressible visor panel tab at least partially covers said at least one screen actuator to adjust said at least one controllable setting upon depression of said at least one integrated depressible visor panel tab.

BRIEF DESCRIPTION OF THE DRAWINGS

FIG. 5A is a cross-sectional view of the visor button shown in FIG. 5 taken along cross-section lines 5A-5A of FIG. 5;

FIG. 5B is a cross-sectional view of the visor button shown in FIG. 5 taken along cross-section lines 5B-5B of FIG. 5;

FIG. 11A is a cross-sectional view of the protective helmet taken along cross-section lines 11A-11A of FIG. 11 showing the interaction between a welding filter and the visor thereof;

DETAILED DESCRIPTION

Figure 1:
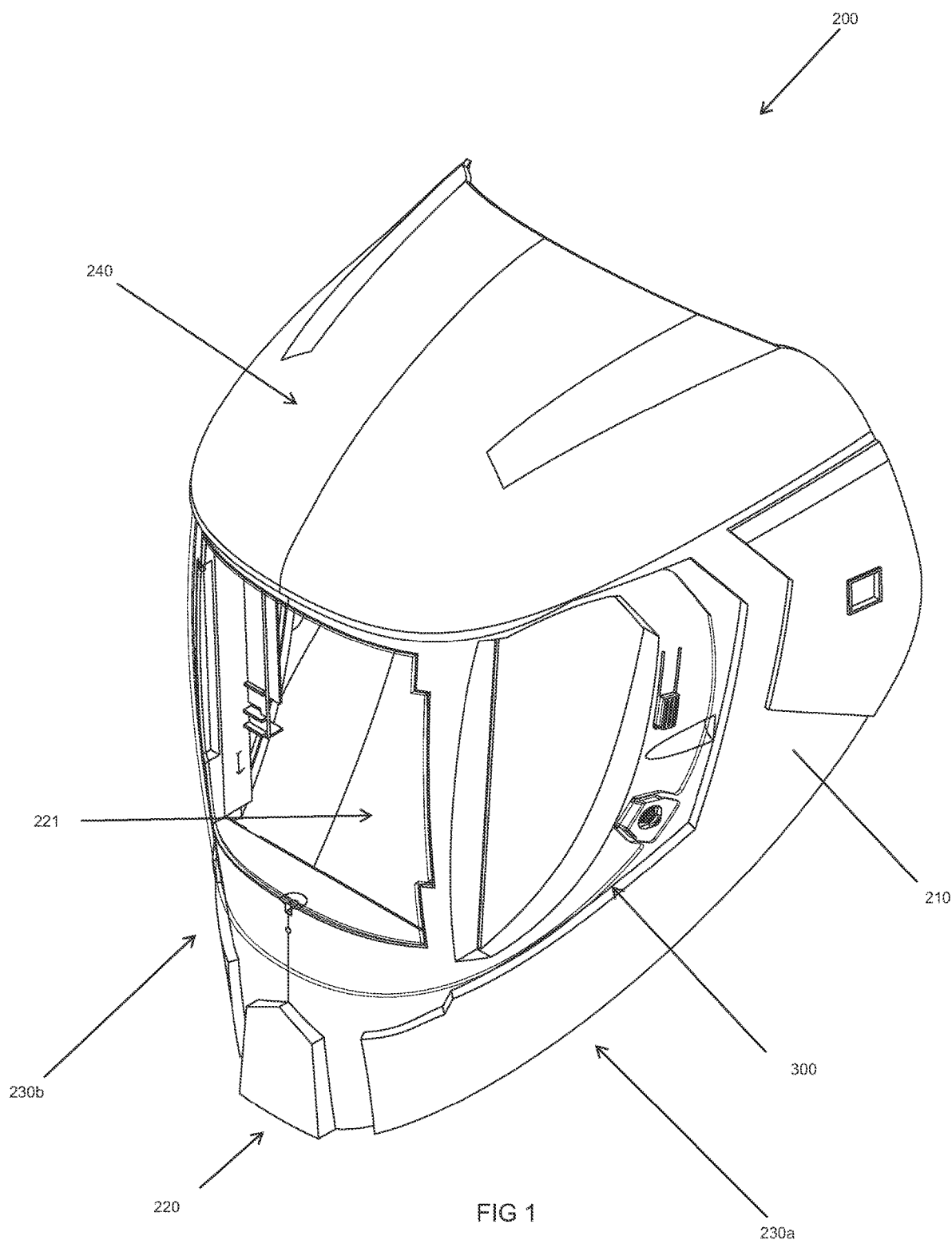
FIG. 1 is a top perspective view of a protective helmet in accordance with one embodiment, comprising a helmet shell and a visor mounted thereto, the protective helmet having a separate button for adjusting a controllable setting thereof.

In the following description, the same numerical references refer to similar elements. Furthermore, for the sake of simplicity and clarity, namely so as to not unduly burden the figures with several references numbers, not all figures contain references to all the components and features, and references to some components and features may be found in only one figure, and components and features of the present disclosure which are illustrated in other figures can be easily inferred therefrom. The embodiments, geometrical configurations, materials mentioned and/or dimensions shown in the figures are optional and are given for exemplification purposes only.

Moreover, it will be appreciated that positional descriptions such as "above", "below", "forward", "rearward", "left", "right" and the like should, unless otherwise indicated, be taken in the context of the figures only and should not be considered limiting. Moreover, the figures are meant to be illustrative of certain characteristics of the head-protecting device and are not necessarily to scale. Unless otherwise stated, the terms inner and outer should be understood with respect to a head-receiving cavity delimited by the helmet shell.

To provide a more concise description, some of the quantitative expressions given herein may be qualified with the term "about". It is understood that whether the term "about" is used explicitly or not, every quantity given herein is meant to refer to an actual given value, and it is also meant to refer to the approximation to such given value that would reasonably be inferred based on the ordinary skill in the art, including approximations due to the experimental and/or measurement conditions for such given value.

In the following description, an embodiment is an example or implementation. The various appearances of "one embodiment", "an embodiment" or "some embodiments" do not necessarily all refer to the same embodiments. Although various features may be described in the context of a single embodiment, the features may also be provided separately or in any suitable combination. Conversely, although the invention may be described herein in the context of separate embodiments for clarity, it may also be implemented in a single embodiment. Reference in the specification to "some embodiments", "an embodiment", "one embodiment" or "other embodiments" means that a particular feature, structure, or characteristic described in connection with the embodiments is included in at least some embodiments, but not necessarily all embodiments.

It is to be understood that the phraseology and terminology employed herein is not to be construed as limiting and are for descriptive purpose only. The principles and uses of the teachings of the present disclosure may be better understood with reference to the accompanying description, figures and examples. It is to be understood that the details set forth herein do not construe a limitation to an application of the disclosure.

Furthermore, it is to be understood that the disclosure can be carried out or practiced in various ways and that the disclosure can be implemented in embodiments other than the ones outlined in the description above. It is to be understood that the terms "including", "comprising", and grammatical variants thereof do not preclude the addition of one or more components, features, steps, or integers or groups thereof and that the terms are to be construed as specifying components, features, steps, or integers. If the specification or claims refer to "an additional" element, that does not preclude there being more than one of the additional element. It is to be understood that where the claims or specification refer to "a" or "an" element, such reference is not to be construed that there is only one of that element. It is to be understood that where the specification states that a component, feature, structure, or characteristic "may", "might", "can" or "could" be included, that particular component, feature, structure, or characteristic is not required to be included.

The descriptions, examples, methods and materials presented in the claims and the specification are not to be construed as limiting but rather as illustrative only. Meanings of technical and scientific terms used herein are to be commonly understood as by one of ordinary skill in the art to which the invention belongs, unless otherwise defined. It will be appreciated that the methods described herein may be performed in the described order, or in any suitable order.

The elements described herein may be applied to any head-protecting device, such as a protective helmet, for instance a welding helmet. For example, the features described herein may be used on the helmet of U.S. Pat. No. 11,129,749.

Figure 2:
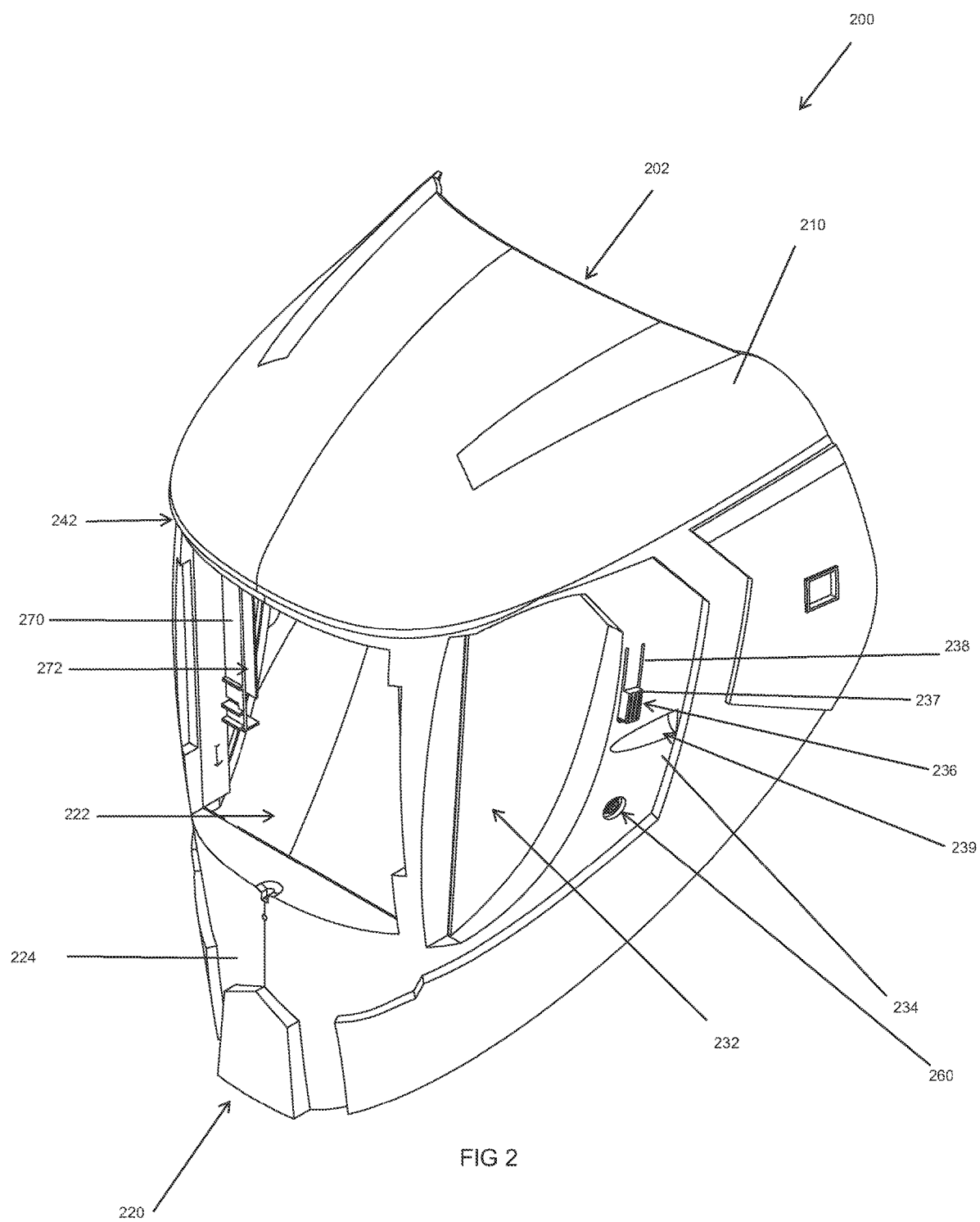
FIG. 2 is a top perspective view of the protective helmet of FIG. 1, with the visor removed from the helmet shell.
Figure 3:
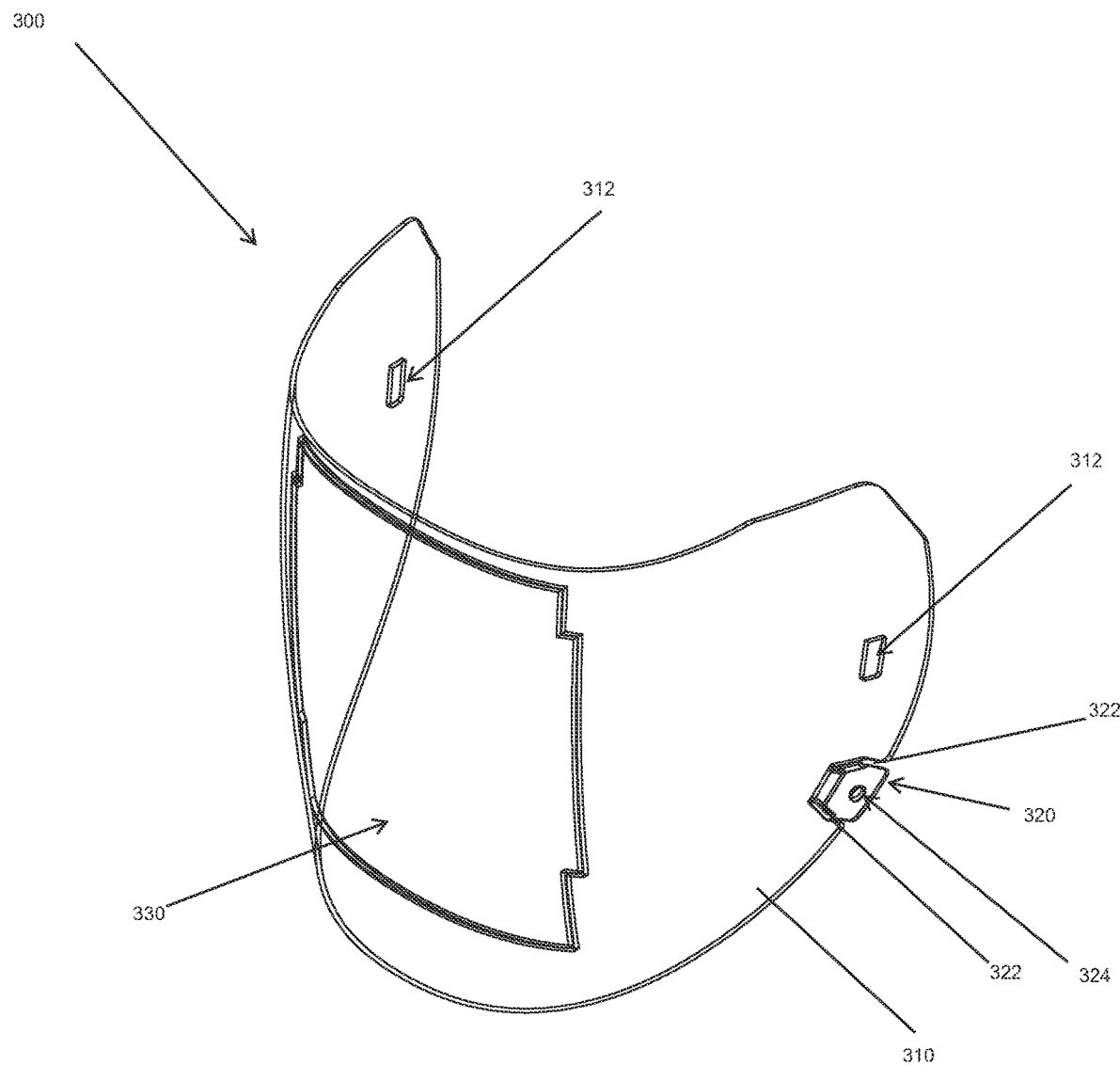
FIG. 3 is an outer perspective view of the visor of FIG. 1.

Referring now to the drawings, and more particularly to FIGS. 1 to 3, there is shown a protective helmet 200 (or head-protecting device 200, for instance a welding helmet 200). In the embodiment shown, the protective helmet 200 comprises a helmet shell 202 at least partially delimiting a head-receiving cavity 221 and a face-protecting member 300 (for instance a visor 300) mounted to the helmet shell (for instance removably mounted thereto). The face-protecting member 300 is thus designed to configure the protective helmet 200 into open and face-protecting/filter-protecting configurations. The protective helmet 200 further comprises an electronic assembly (for instance, but without being limitative, comprising an electronic control system and an auto-darkening welding filter) mounted to the helmet shell 202 and having at least one controllable setting. As detailed below, the face-protecting member 300 comprises at least one panel tab 320 (or at least one depressible visor button 320) selectively depressible to cooperate with an actuator mounted to or formed integral with the helmet shell 202 or the electronic assembly and operatively coupled to the electronic assembly to adjust said at least one controllable setting upon depression of said at least one panel tab.

In other words, as detailed below, the head-receiving cavity 221 forms a see-through opening 222 in the helmet shell 202. In the embodiment shown, the electronic assembly (not shown) comprises a welding filter mounted to the helmet shell 202 and covering at least partially the see-through opening, the welding filter having the at least one controllable setting. In the embodiment shown, the electronic assembly further comprises an electronic control system configured to allow adjustment of said at least one controllable setting of the welding filter. In the embodiment shown, the at least one depressible visor button 320 is formed integrally with the visor 300. In the embodiment shown, the actuator 260 (or filter actuator 260) is mounted to or formed integral with the helmet shell and operatively coupled to the electronic control system. The actuator 260 may alternatively be mounted to or formed integral with the welding filter and operatively coupled to the electronic control system to adjust the at least one controllable setting of the welding filter. The at least one depressible visor button 320 is configured to cooperate with the filter actuator upon being pressed, allowing a user to adjust said at least one controllable setting of the welding filter.

In yet other words, the visor button 320 comprises an integrated depressible visor panel tab 320 formed by cutting a pattern into the visor 300. The filter actuator 260 (or screen actuator 260) is formed integral with or mounted to the shell 202, or alternatively formed integral or mounted to the welding filter, and operatively coupled to the electronic control system to control said at least one controllable setting upon actuation thereof. The electronic control system may comprise a circuit board allowing for adjustment of the at least one controllable setting. The at least one depressible visor panel tab 320 at least partially covers the screen actuator 260 to adjust the at least one controllable setting upon depression of said at least one depressible visor panel tab 320. The visor 300 accordingly allows a user to change the at least one controllable setting without having to remove the visor from the helmet. The visor 300 additionally provides protection to the screen actuator 260 from dust, dirt, or other contaminants.

In the embodiment shown, the electronic assembly comprises the above-mentioned auto-darkening welding filter, but it could be conceived for head-protecting devices comprising any other type of electronic assembly. For instance, electronic assemblies comprising an audio system or an electronic air filtering system may similarly be used.

Helmet Shell

In the embodiment shown, the helmet shell 202 (or head-protecting shell 202 or head-receiving shell 202) at least partially delimits the above-mentioned head receiving cavity 221 for receiving the head of the user, while the visor 300 protects the face of the user as well as at least partially the shell 202 and/or the auto-darkening welding filter mounted to the helmet shell 202. More particularly, the face-protecting member 300 is shaped and dimensioned to substantially cover the see-through opening 222 formed in the helmet shell 202 when the visor is in the closed configuration and to substantially cover the auto-darkening welding filter extending at least partially in the see-through opening 222.

The shell 202 comprises a shell body 210, the shell body 210 having a front portion 220, first and second side portions 230*a*, 230*b*, and a top portion 240. The front portion 220 comprises the front see-through opening 222 and a front view recess 224 adjacent thereto (formed in the helmet shell 202 below the see-through opening 222, in the embodiment shown).

Only the first side portion 230*a* will be described in the following and given that the second side portion 230*b* is identical to the first side portion 230*a*, any description applies to both sides, with the reference numeral 230 being used. The head-receiving cavity forms a side see-through opening 232 in the side portion 230 of the helmet shell. A side recess 234 is also formed in the side portion 230 of the helmet shell 202, adjacent thereto (for instance rearwardly thereof, considered with respect to the front see-through opening 222). The front view see-through opening 222 is arranged between the side see-through openings 232 formed in the first and second side portions 230*a*, 230*b*.

Viewed from an exterior of the head-protecting device 200, the side and front recesses 224, 234 are sized and shaped to at least partially receive the visor 300 thereon so that when the visor 300 is received in said recesses and when the protective helmet 200 is configured in the closed configuration, an edge 242 of the top portion 240 of the helmet 200 slightly protrudes outwards relative to the visor 300, providing physical protection to the visor 300 (e.g., in case of a drop). That is to say, the visor 300 is substantially inwardly offset with regards to an outer surface of a remaining portion of the helmet shell 202 bordering the recesses and openings formed in the helmet shell 202.

In the illustrated embodiment, the head-protecting device 200 further includes a locking mechanism 236 for locking and unlocking the helmet shell 202 to the visor 300. In the embodiment shown, a finger recess 239 is formed in the helmet shell 202, for instance in the side recess 234. The filter actuator comprises a depressible side shell-mounted button 260 mounted (for instance resiliently) to the helmet shell 202, for instance to the side recess 234 thereof, to an outer surface thereof.

In the embodiment shown, the locking mechanism 236 comprises a depressible button mounted to one of the helmet shell and the visor, and a corresponding button-receiving aperture formed in the other one of the helmet shell and the visor for receiving the depressible button when the locking mechanism is configured in a locked configuration.

In the embodiment shown, the locking mechanism 236 comprises a depressible button 237 mounted (for instance resiliently) to the helmet shell 202 (for instance to the side portion 230 thereof), the depressible button 237 being configured to be received in a corresponding aperture 312 formed in the visor 300. In the embodiment shown, the depressible button 237 is a protrusion extending outwardly from the side recess 234, with two adjacent and parallel slots 238 being cut into the helmet shell 202 to allow for the button 237 to be resiliently pressed. The depressible button 237 and corresponding visor aperture 312 are operably coupled to selectively lock or unlock the visor 300 to/from the shell 202 upon engagement of the depressible button 237 with the button-receiving visor aperture 312.

Although in the illustrated embodiment, the depressible button 237 is mounted on the shell 202 and the visor aperture 312 is formed in the visor 300, it is equally envisaged that other configurations may be used. The depressible button 237 can therefore be mounted to one of the helmet shell 202 and the visor 300, and a corresponding button-receiving aperture formed in the other one of the helmet shell and the visor for receiving said depressible button when the locking mechanism is configured in a locked configuration.

The finger recess 239 is also found on the side recess 234 and is shaped and sized to allow a finger of a user to slip therein for displacing the visor 300 relative to the helmet shell 202 (for instance to remove it therefrom) after unlocking the visor 300 from the shell 202 (i.e., after configuring the locking mechanism in an unlocked configuration). In the embodiment shown, the finger-receiving recess 239 is at least partially covered by the visor 300, positioned near to a substantially vertical edge bordering the side recess 234 to produce a finger-receiving gap (or nail-receiving gap) between the visor 300 and the edge of the side recess 234, allowing a user to manipulate the edge of the visor 300 from between the visor and the shell 202.

As best shown in FIG. 2, as mentioned above, the actuator 260 (for instance the filter actuator) comprises the depressible shell-mounted button 260 discretely mounted onto the helmet shell 202 and operatively coupled, as detailed below, to the at least one visor button 320.

The depressible side shell-mounted button 260 is also positioned on the side recess 234, for instance near to a bottom edge of said recess. In the embodiment shown, the side shell-mounted button 260 is a button assembly, comprising a depressible side shell button member, a resilient member and a button-receiving platform for mounting onto the helmet shell 202 (for instance through an adhesive). Other fixing means may be used to secure the shell-mounted button 260 to the helmet shell. In the embodiment shown, the resilient member is depressibly connected to the button receiving platform mounted onto the shell 202, biasing the button member to return to its normal state after being pushed. In other words, the side shell-mounted button 260 is configurable into a depressed state, when a pressure is applied on the button member thereof, either directly or indirectly, by a user. The side shell button 260 is further configurable into a deployed state (or extended state or unactuated state) when no pressure is applied on the button member thereof.

It is appreciated that the shape, the configuration, and the location of the actuator can vary from the embodiment shown.

Figure 9:
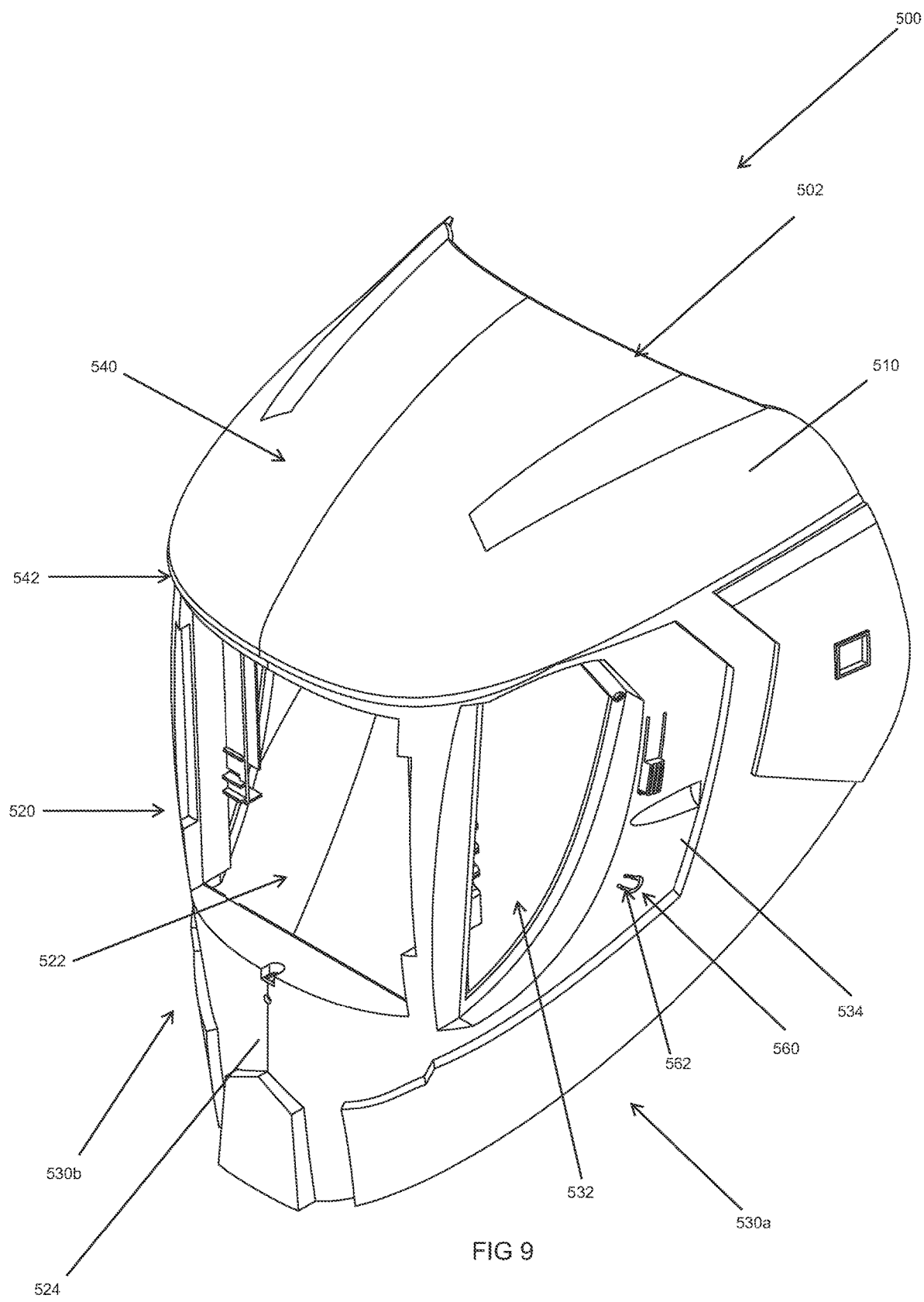
FIG. 9 is a top perspective view of a protective helmet in accordance with another embodiment, the protective helmet having an integrally formed button for adjusting a controllable setting thereof.
Figure 10:
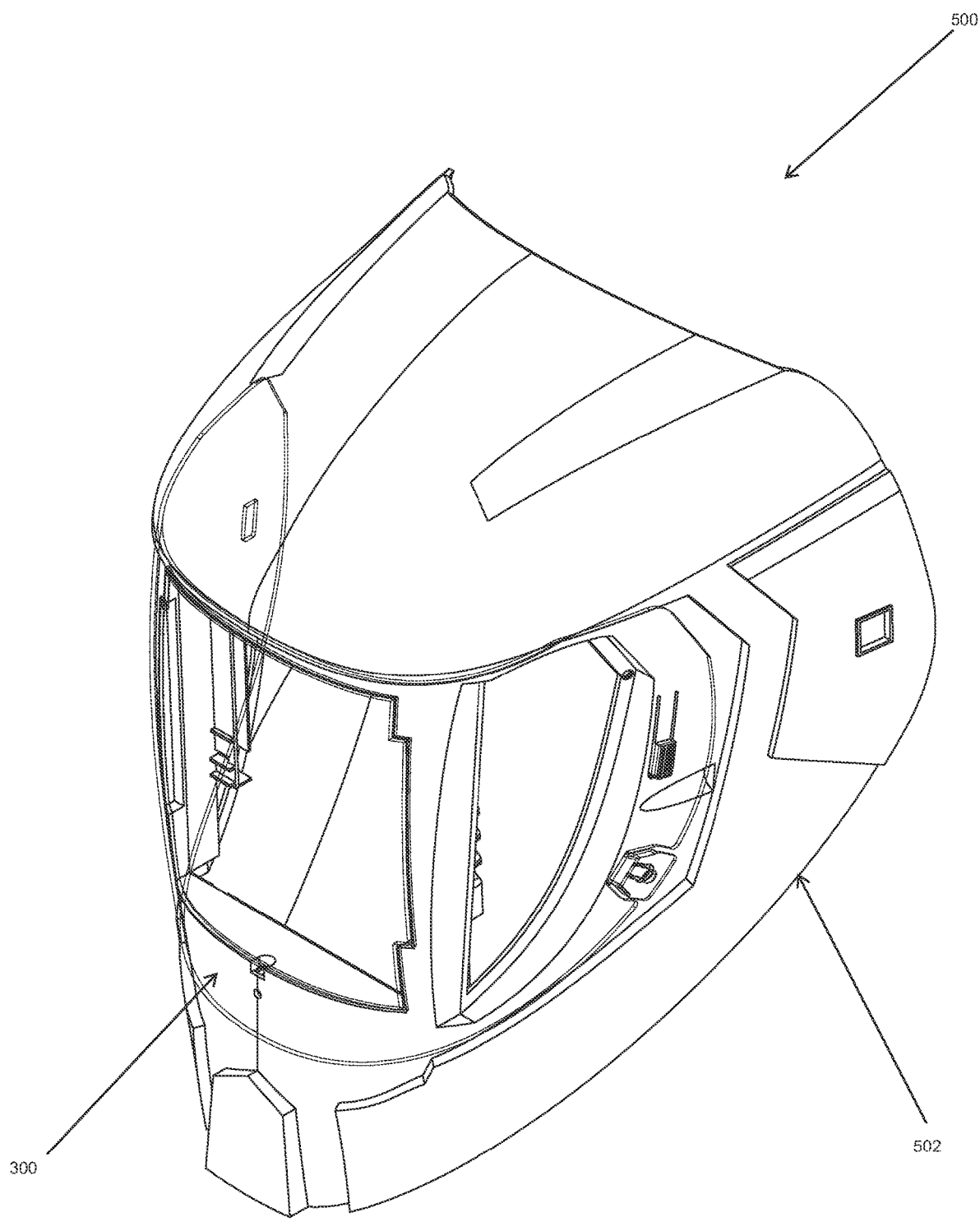
FIG. 10 is a partially transparent top perspective view of the protective helmet of FIG. 9, with a visor mounted on the helmet shell.

For instance, as represented in FIGS. 9 and 10, it could be conceived as a filter actuator (or actuator) comprising a shell tab formed integral with the helmet shell and operatively coupled to the visor button. With reference to FIGS. 9 and 10, there is shown a second embodiment of a helmet. The helmet 500 comprises a helmet shell 502 and the visor 300. The helmet 500 is similar to the helmet 200 of the first disclosed embodiment, however in the second embodiment the helmet shell 502 comprises a tab formed as part of the shell, similar to the helmet described in U.S. Pat. No. 11,129,749.

The helmet shell 502 comprises a shell body 510, the shell body 510 having a front portion 520, first and second side portions 530a, 530b, and a top portion 540. As previously stated for the first embodiment of the helmet 200, only side portion 530a will be described in the following and given that side portion 530b is identical to side portion 530a, any description applies to both sides, with the reference numeral 530 being used. The head-receiving cavity forms a side see-through opening 532 in the side portion 530 of the helmet shell. A side recess 534 is also formed in the side portion 530 of the helmet shell, adjacent thereto (for instance rearwardly thereof, considered with respect to front see-through opening 522). The front view see-through opening 522 is arranged between the side see-through openings 532.

Viewed from an exterior of the helmet 500, the side and front recesses 534, 524 are sized and shaped to receive the visor 300 thereon so that when the visor 300 is received in said recesses, an edge 542 of the top portion 540 of the helmet 500 slightly protrudes outwards relative to the visor 300, providing physical protection to the visor 300 (e.g., in case of a drop). That is to say, the visor 300 is substantially inwardly offset with regards to an outer surface of a remaining portion of the helmet shell 502 bordering the recesses and openings formed in the helmet shell 502.

Unlike the helmet 200, wherein the shell button 260 is mounted to the helmet shell for actuating a circuit board mounted inside the shell 202, in the second embodiment, the actuator comprising a shell tab 560 is formed integral with the helmet shell 502. The tab 560 is cut into the helmet shell and comprises a tab cutout 562 which is largely U-shaped. The tab 560 is resiliently depressible, and similar to the shell button 260, may be operably connected to a circuit board mounted inside of the shell 502 for adjusting settings of the auto-darkening filter.

Figure 11:
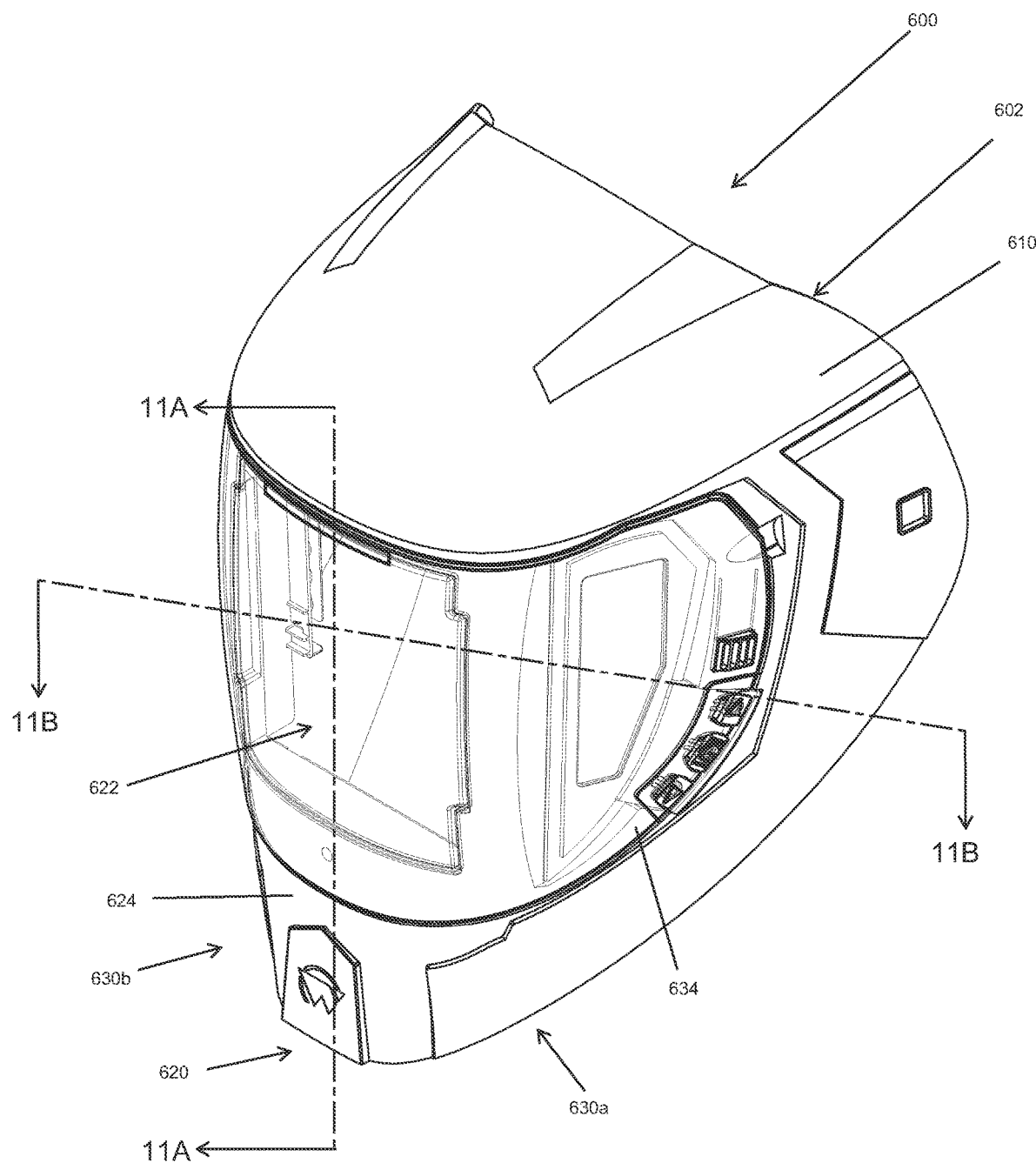
FIG. 11 is a top perspective view of a protective helmet in accordance with another embodiment, the protective helmet comprising a helmet shell and a visor mounted thereto and having multiple buttons for adjusting controllable settings thereof.
Figure 12:
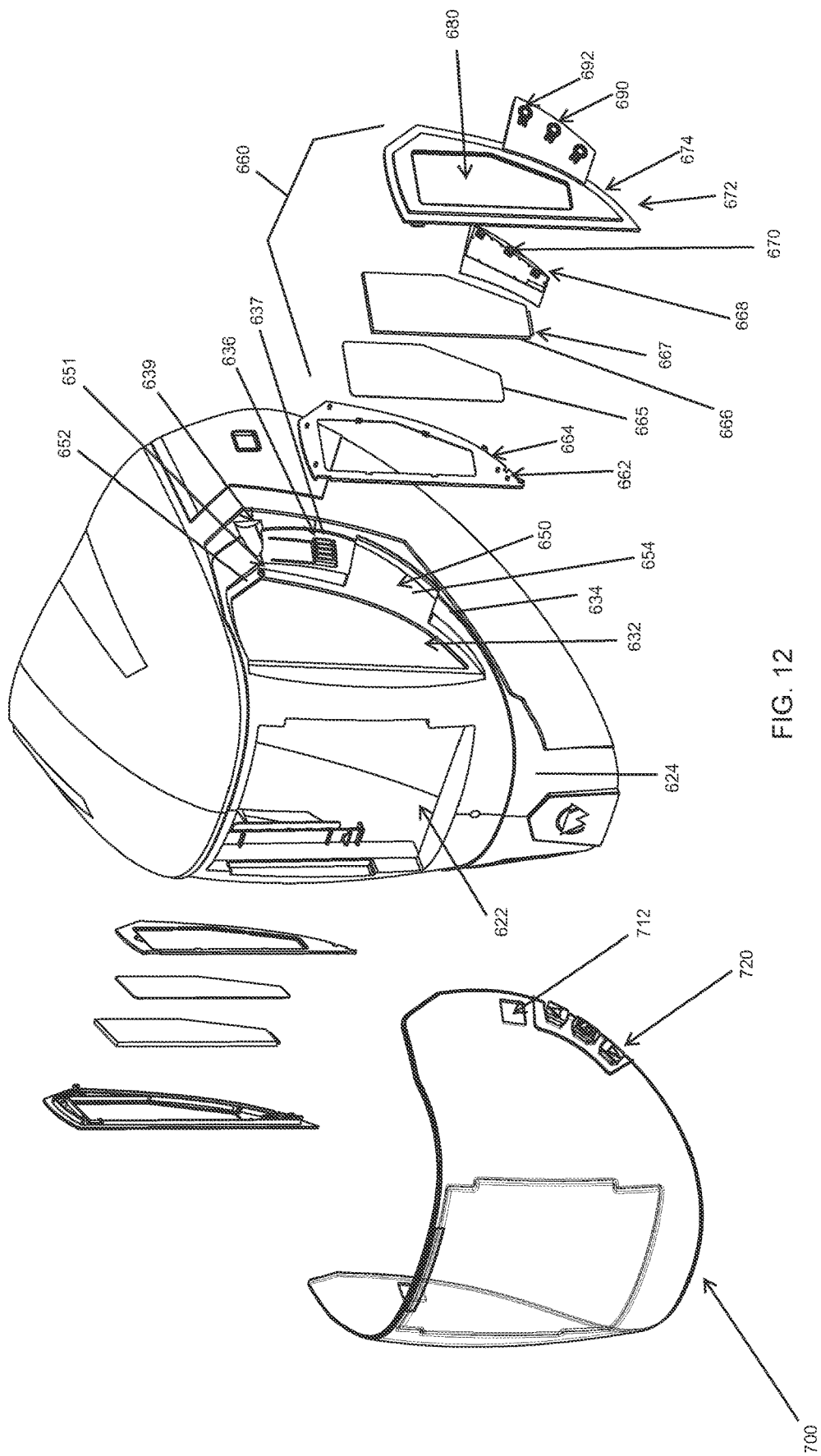
FIG. 12 is a partially exploded view of the protective helmet of FIG. 11 showing each of the individual parts.

With reference to FIGS. 11 to 12, there is shown a third embodiment of a helmet. The helmet (or head-protecting device or protective helmet) 600 comprises a helmet shell 602 substantially similar to the helmet shells 202, 502 of the helmets 200, 500. In the embodiment shown, the helmet shell 602 at least partially delimits a head-receiving cavity 604 and a face-protecting member 700 (for instance a visor 700) mounted to the helmet shell (for instance removably mounted thereto) to configure the helmet into open and closed configurations. The helmet 600 is similar to the helmet 200 in that at least one visor button, three visor buttons 720 in the illustrated embodiment, are formed integrally with the visor 700 and the visor buttons 720 cooperate with an electronic control system configured to allow adjustment of a controllable setting upon being pressed, allowing a user to adjust at least one controllable setting.

The helmet shell 602 comprises a shell body 610, the shell body 610 having a front portion 620, first and second side portions 630a, 630b (side portion 630 refers to either). The front portion 620 comprises the front see-through opening 622 and a front view recess 624 adjacent thereto (formed in the helmet shell 602 below the see-through opening 622, in the embodiment shown).

In the illustrated embodiment, a side recess 634 is also formed in the side portion 630 of the helmet shell 602, adjacent thereto (for instance rearwardly thereof, considered with respect to the front see-through opening 622). The front view see-through opening 622 is arranged between the side see-through openings 632 formed in the first and second side portions 630a, 630b. Similar to the helmet 200, the helmet 600 also includes a locking mechanism 636 for locking and unlocking the helmet shell 602 to visor 700. In the embodiment shown, a finger recess 639 is formed in the helmet shell 602, for instance in the side recess 634. The locking mechanism 636 comprises a depressible button 637 mounted (for instance resiliently) to the helmet shell 602 (for instance to the side portion 630 thereof), the depressible button 637 being configured to be received in a corresponding aperture 712 formed in the visor 700.

There is further a side section 650 in the side recess 634, the side section 650 being recessed relative to the side recess 634 and comprising a peripheral side section 652 and a rectangular side section 654. The side section 650 is shaped and dimensioned to receive a button assembly 660. The button assembly 660 comprises an inner frame 662, the frame being shaped and dimensioned to be received in the peripheral side section 652. The frame further comprises apertures 664 which, when placed in the peripheral side section 652, align with corresponding apertures 651 in the peripheral side section 652. Fasteners, such as screws or nuts and bolts, may then be placed in the apertures 651 to removably fasten the inner frame 662 to the helmet 600. The button assembly 660 further comprises a side screen 666. The side screen 666 may have an auto-darkening filter configured to selectively switch between a light state and a dark state, for example to block out light. The side screen 666 may accordingly be operably coupled to the electronic control system for changing a controllable setting of the side screen 666. The side screen 666 may alternatively be transparent and allow for the user to see therethrough, for example if the visor mounted onto the helmet 600 has a transparent side portion coincident with the side screen 666. In the illustrated embodiment, a back cover plate 665 protects an inner face of the side screen 666 while the visor 700 protects an outer face of the side screen 666 (see FIG. 12). The back cover plate 665 may, for example, protect the inner face of the side screen 666 from contaminants, such as spills or welding splatter, if the helmet 600 is removed from the head of the user when not in use. The side screen 666 is mounted adjacent to an actuator panel 668. The actuator panel 668 is sized and shaped to be received in the rectangular side section 654. The actuator panel 668 comprises actuators or buttons 670, three in the illustrated embodiment, coupled to corresponding switches on a circuit board mounted onto the helmet 600, such as inside the helmet shell 602.

The button assembly further comprises an outer frame 672 having a frame section 674 and a button panel 690. In the illustrated embodiment, the button panel 690 is formed integral with the outer frame 672. Alternatively, the button panel 690 may be mounted on the outer frame 672 or the helmet shell 602, for example with fasteners. The frame section 674 is sized and shaped to be received in the peripheral side section 652, while the button panel 690 is sized and shaped to be received in the rectangular side section 654 of the helmet shell 602. The frame section 674 and the button panel 690 may be integrally formed together, alternatively they may be formed as separate parts. The frame section 674 comprises an inner face facing towards the helmet shell 602 and an opposed outer face facing outwardly, as well as a viewing aperture 680. The inner face comprises sleeves for receiving fasteners therein, in one embodiment being threaded for receiving screws, to secure the outer frame 672 to the inner frame 662.

The frame section 674 further comprises a seat for receiving the side screen 666 thereon. In the illustrated embodiment, the seat comprises two protrusions from opposing sides of the frame section 674 mounted under the viewing aperture 680. The side screen 666 comprises a protrusion 667 which is received between the opposing sections of the seat and positions the side screen 666 with respect to the outer frame 672. The side screen 666 further comprises a flange which is received in the outer frame 672 and the inner frame 662. Accordingly, when the outer frame 672 is fastened to the inner frame 662, the back cover plate 665 and side screen 666 are locked in position between the outer frame 672 and the inner frame 662, securing the entirety of the button assembly 660 to the helmet shell 602. The button panel 690 comprises tabs 692, three in the illustrated embodiment, which are positioned over the buttons 670. When the tabs 692 are pressed, they in turn press the buttons 670, which then interact with the circuit board mounted in the helmet shell 602 to allow the user to adjust one or more controllable settings of the helmet 600, such as the shade/darkness of the visor mounted onto the helmet shell 602. Alternatively, the tabs 692 may be removed entirely. Alternatively, the tabs 692 and/or buttons 670 may be formed integral with the helmet 600, for example in the rectangular side section. The button assembly 660 is configured to be used with visor 700 but may also be compatible with other visors.

Face-Protecting Member/Visor

With reference to FIGS. 1 and 3 and as already described, the visor 300 (or face-protecting member 300 or filter-protecting member 300) is at least partially received in the front and side recesses 224, 234 formed in the helmet shell 202 and configured to be attached (for instance removably) to the shell 202, so as to selectively configure the helmet into open and closed configurations.

The visor 300 comprises a visor body 310 and a front vision port 330. The visor body 310 has a generally half cylindrical profile and comprises the above-described visor-locking apertures 312 (or shell-mounting apertures 312). Alternatively, the visor body 310 may be any other shape which would be configured to fit with the shell 202 and to substantially cover the see-through opening thereof and/or the auto-darkening welding filter mounted thereto when the helmet is in the closed (or face-protecting or filter-protecting) configuration.

The visor apertures 312 (or visor-locking apertures) are positioned on opposing sides of the visor body 310 and configured to be operably coupled to the button 237 when fitted onto the shell 202, allowing the visor 300 to lock onto the shell 202 (i.e., when the locking mechanism is in the locked configuration). The vision port 330 is a segment of a front portion of the visor body 310 which may be more transparent than the remainder of the visor body 310, allowing the user to see-through clearly. Alternatively, the visor 300 may have a visor body 310 with constant opacity throughout and no vision port 330. In the embodiment shown, the visor 300 is shaped and dimensioned so that the vision port thereof substantially faces the auto-darkening welding filter mounted to the helmet shell.

The visor 300 further includes the above-mentioned visor button 320 (or depressible visor panel tab or depressible visor button). The visor button 320 is a resiliently depressible button or tab that is sized and shaped to be received over (for instance to substantially cover) the depressible side shell button 260. Similarly to the side shell button 260, the visor button 320 is a protrusion extending outwardly from the visor body 310 with two slots 322 (for instance substantially parallel to each other) cut into the visor body 310 and adjacent to and substantially bordering the button 320, allowing the visor button 320 to be resiliently depressed with respect to the visor body 310. This may additionally facilitate locating of the visor button 320 during use. The visor button 320, unlike the side shell button 260, is accessible to the user when the visor 300 is mounted to the helmet shell 202.

Figure 5:
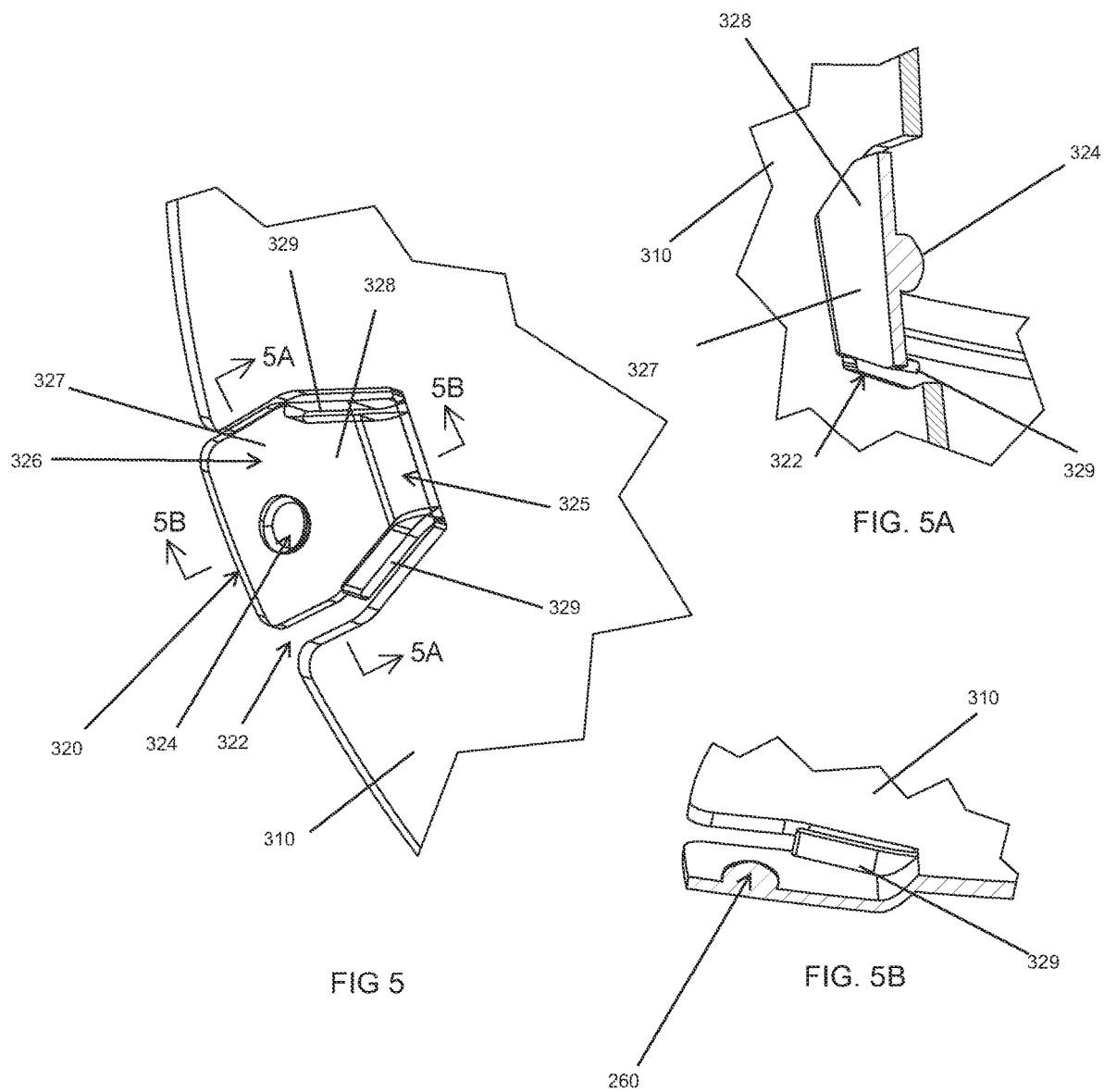
FIG. 5 is a close-up view of a visor button of the visor of FIG. 3.
Figure 6:
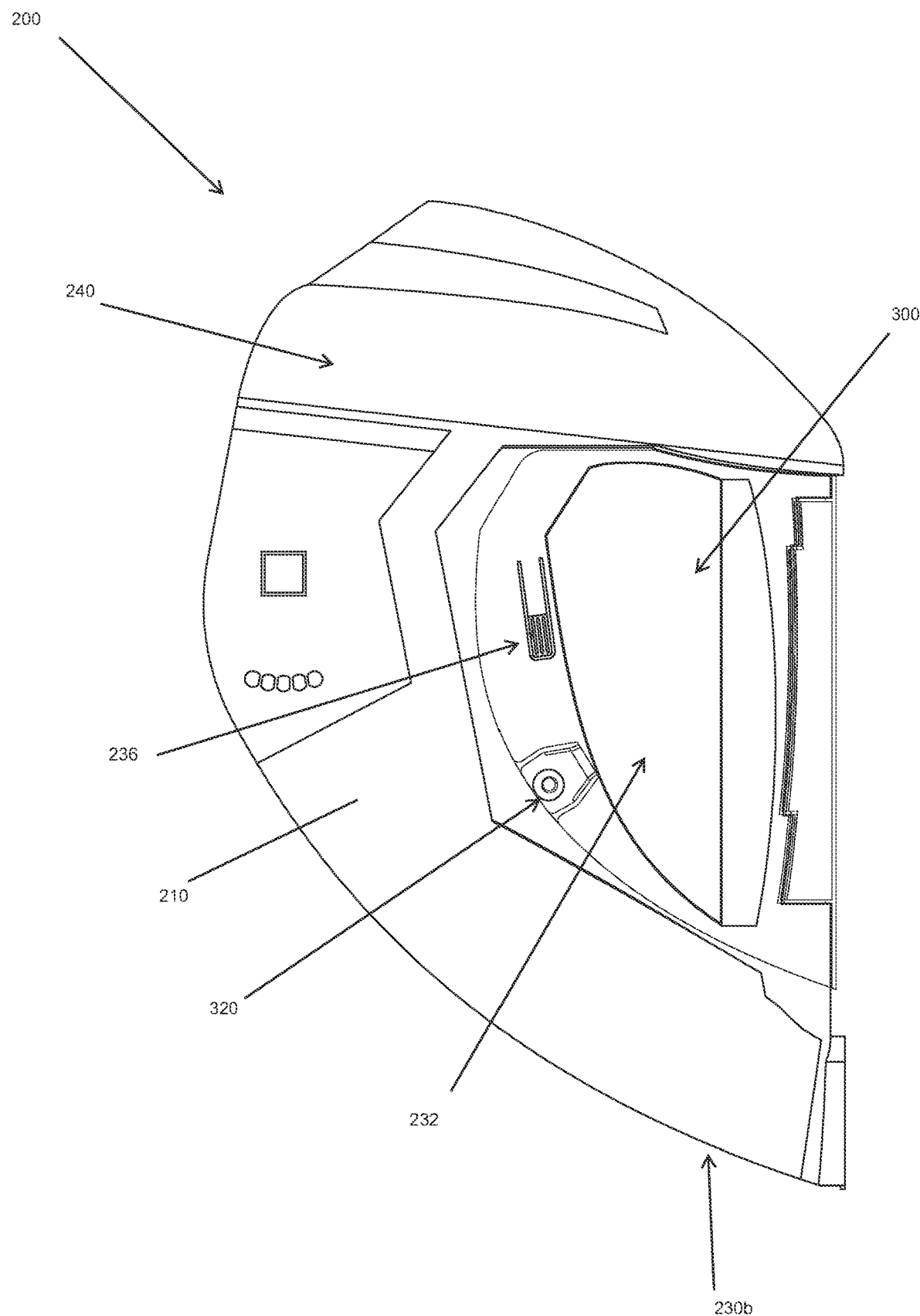
FIG. 6 is a side elevational view of the helmet of FIG. 1.
Figure 7:
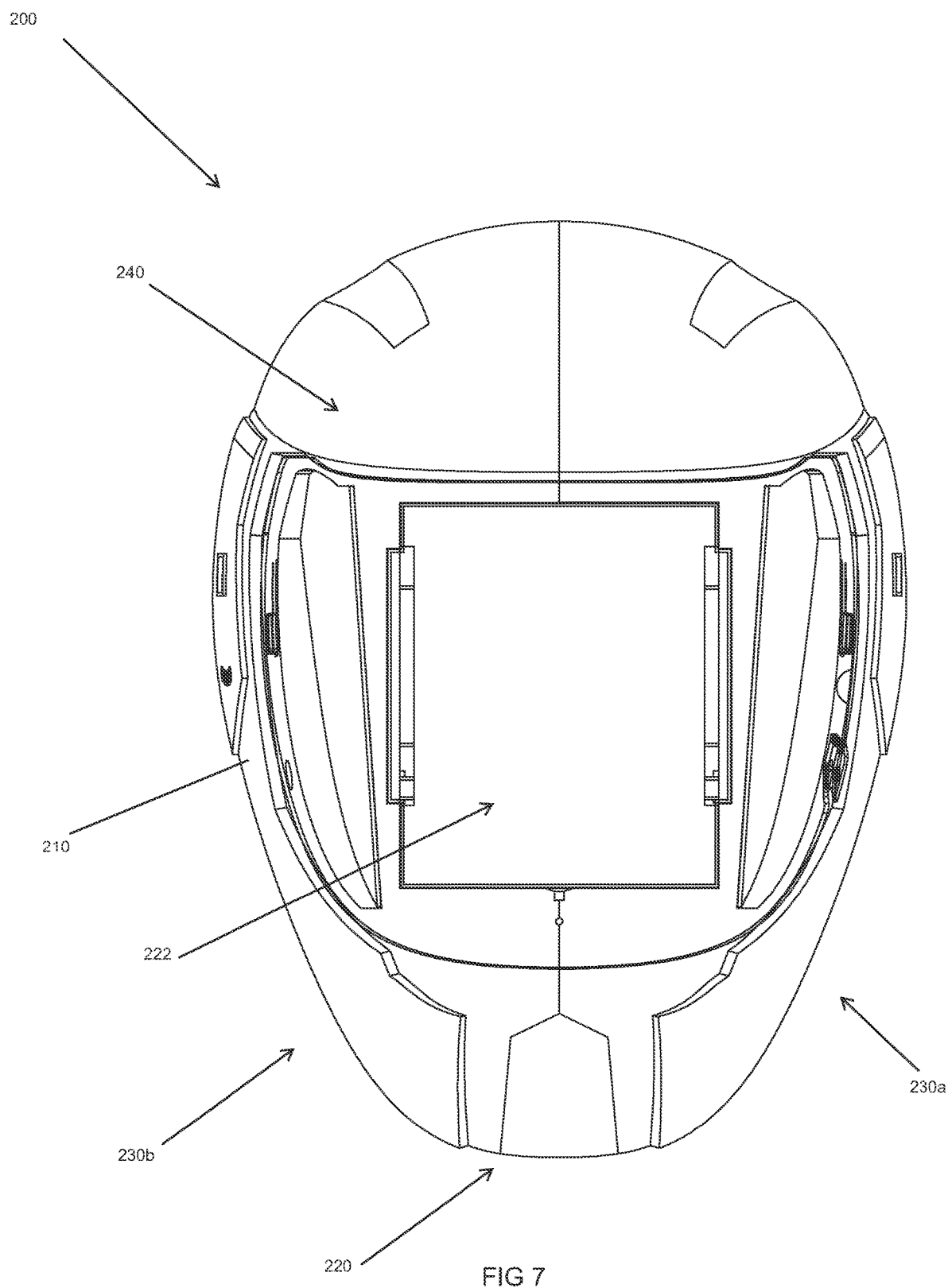
FIG. 7 is a front elevational view of the helmet of FIG. 1.
Figure 8:
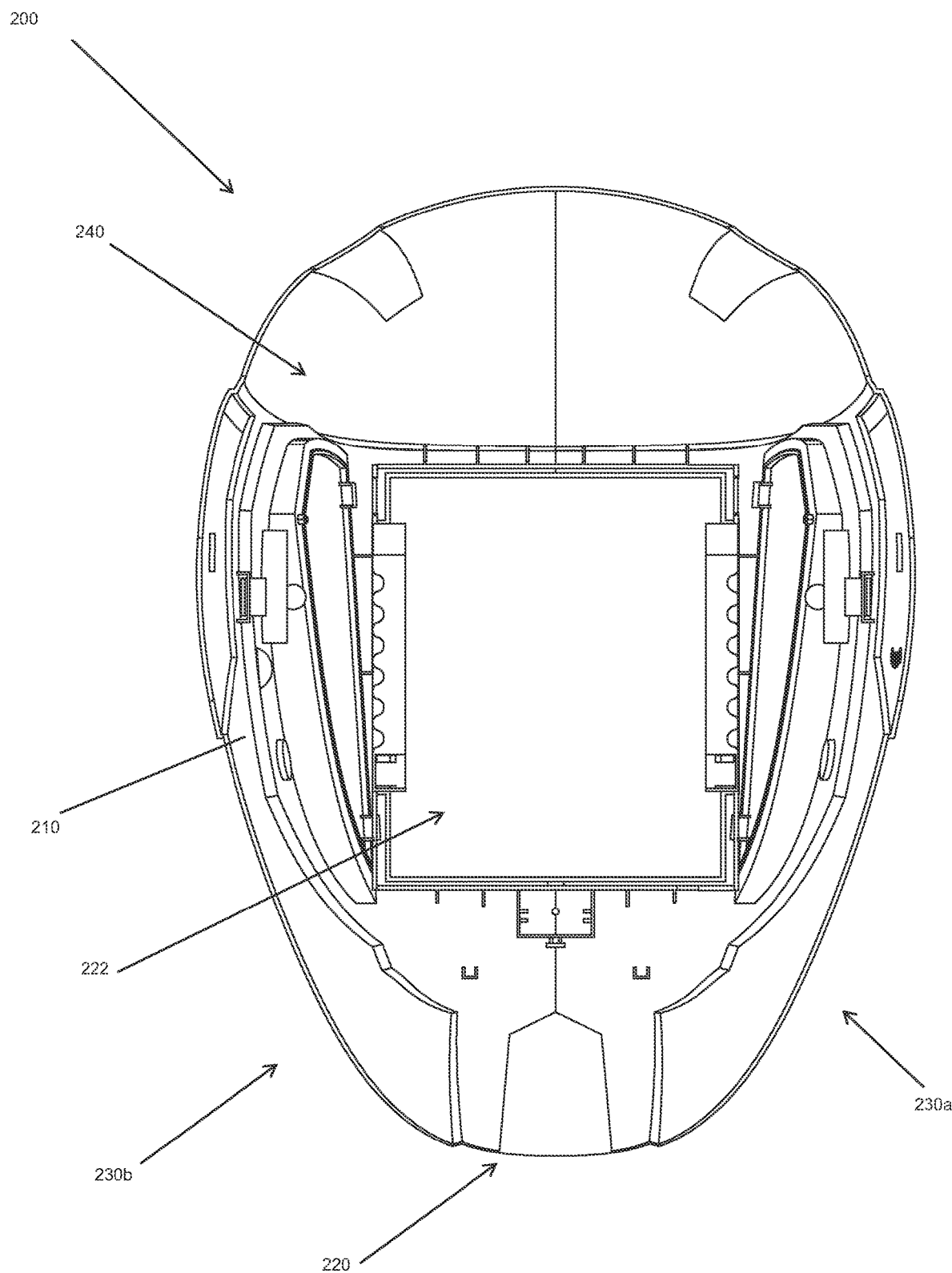
FIG. 8 is a rear elevational view of the helmet of FIG. 1.

As best shown in FIGS. 5, 5A and 5B, the visor button 320 further includes a nipple 324 thereof positioned centrally on a button body. The button 320 is thus shaped and dimensioned so that the side shell button 260 is in communication with the nipple 324. It could however be conceived as a visor button with no nipple formed therein.

Figure 4:
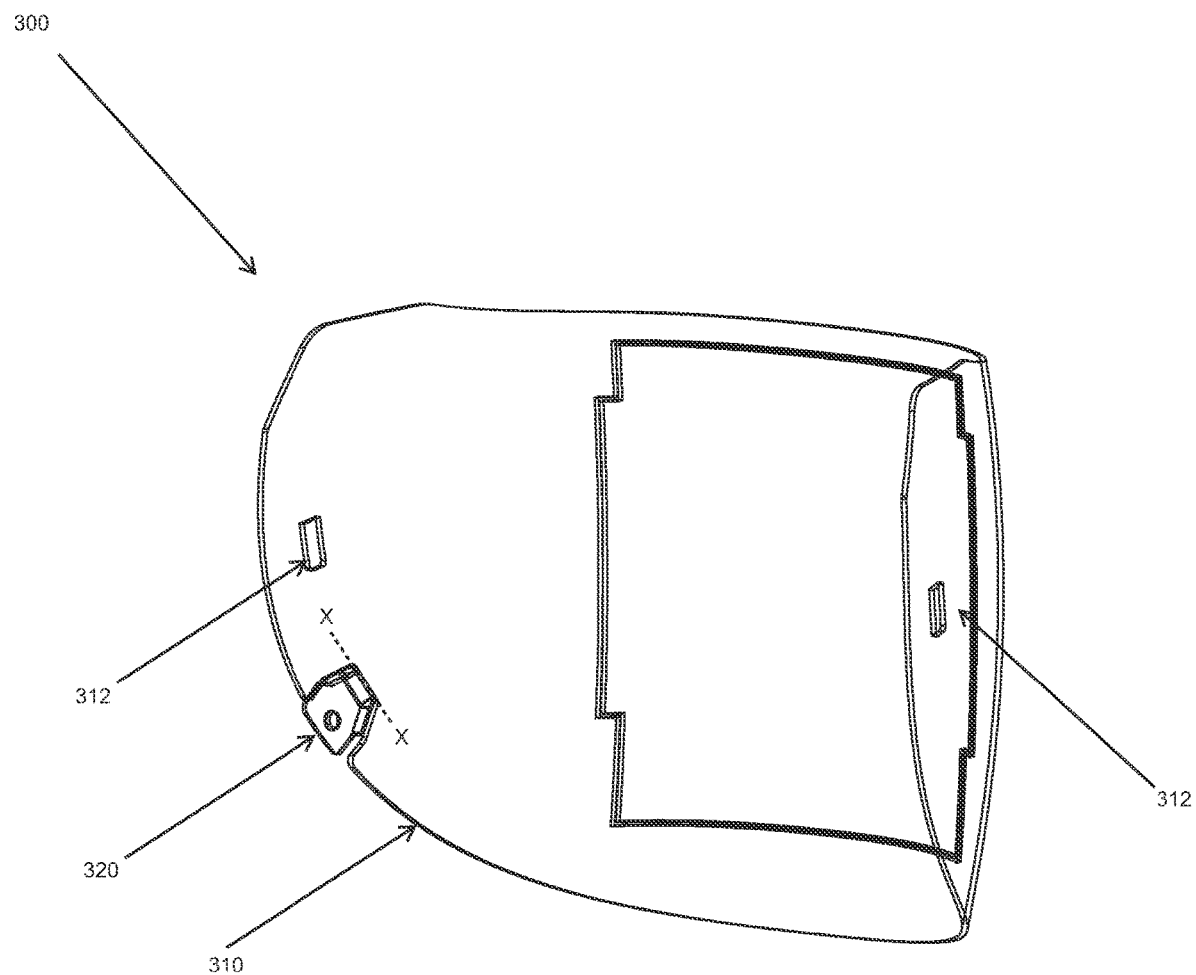
FIG. 4 is an inner perspective view of the visor of FIG. 3.

With reference to FIGS. 4-5B, the visor button 320 is shown in greater detail. The visor button 320 is formed integral with the visor body 310 and comprises the above-mentioned nipple 324 formed centrally in the depressible member 326 (or button body 326) of the visor button 320. The slots 322 at least partially bordering the depressible member 326 of the visor button 320 create gaps between the button and the visor body 310. The visor button 320 comprises a connecting member 325 forming a flexible junction between the depressible member 326 and the visor body 310. The connecting member 325 defines a step which connects the depressible member 326 to the visor body 310, allowing it to pivotally move with respect to the same. The connecting member 325 further defines a pivoting axis X-X (FIG. 4) which substantially corresponds to the axis where the connecting member 325 connects to the visor body 310. Although in the illustrated embodiment the step is sloped with respect to a surface defined by a portion of the visor body to which the visor button is connected, it is envisaged that it could similarly be any other shape, such as a 90-degree step.

The depressible member 326 has a substantially rectangular section 327, and a tapered section 328 which tapers towards the connecting member 325. The tapered section 328 comprises, in the embodiment shown, two side walls 329 placed on opposing sides of the tapered section 328 and extending inwardly with regards to the head-receiving cavity. The tapered section 328 comprises an actuation face forming a continuity with an actuation face of the substantially rectangular section 327 of the depressible member 326, an opposed inner face, the two side walls 329 extending from the inner face of the tapered section 328 which extend outwardly from the visor body 310, adjacent to the slots 322. In other words, the actuation faces of the rectangular section 327 and the tapered section 328 (forming together an actuation face of the depressible member 326) extend, when no pressure is applied to the button body 326, substantially parallel to the surface defined by the portion of the visor body to which the visor button is connected and is spaced apart therefrom. In other words, the actuation face of the depressible member 326 is offset with respect to the surface defined by the portion of the visor body 310 to which the visor button 320 is connected, the connecting member 325 and the two side walls 329 of the tapered section 328 extending between the actuation face of the depressible member 326 and the surface defined by the portion of the visor body 310 to which the visor button 320 is connected.

In the illustrated embodiment, the side walls 329 extend approximately half a length of the depressible member 326 and across an entirety of the tapered section 328, though other configurations and lengths may be desired. The side walls 329 provide additional strength to the depressible member 326.

In the embodiment represented in FIGS. 9 and 10 wherein the filter actuator comprises the shell tab 560 formed integral with the helmet shell 502 and operatively coupled to the visor button 320, the visor button 320 is resiliently depressible and sized and shaped to be received substantially over the shell tab 560 when placed on the shell 502. By pressing the visor button 320, the tab 560 is actuated which then further actuates a switch on the circuit board for controlling a setting of the auto-darkening filter.

It is appreciated that the shape, the configuration, and the location of the visor button 320 can vary from the embodiment shown. For instance, it could be conceived as a depressible member with no side walls, or with side walls having any other shape and/or dimension. Additionally, although the visor button 320 has been shown as a single button in the illustrated embodiments, it is equally envisaged that the button may instead be a plurality of buttons for interacting with a plurality of buttons mounted to and/or formed integral with the helmet shell, each one for adjusting a desired setting, as described below. For instance, the plurality of visor buttons could toggle through a selection of modes, such as shade, sensitivity, delay, work time, or other functions that can be programmed into an adjustable-darkness helmet, for example displaying an interface equivalent to a heads up display. Sensitivity may be the sensitivity of the auto-darkening welding filter to light which would trigger a change of the auto-darkening filter from a light-state to a dark-state. Shade may be the amount of light that is configured to be filtered out by the auto-darkening filter. Delay may be the amount of time that light may be permitted to pass through the auto-darkening welding filter after a threshold amount of light has been exceeded, prior to changing from a light-state to a dark-state. One of the visor buttons could, for instance, increase a value for a selected mode, while another one could decrease the value for the selected mode, and another button could select a specific mode or be used to switch through modes until the desired mode is selected. Furthermore, while the visor button has been formed integrally with the visor in the illustrated embodiments, it is equally envisaged that the visor button may be formed separately from the visor and/or including for instance different material from the visor body.

With reference to FIGS. 11 to 12, there is shown another embodiment of a visor. The visor 700 is substantially similar to the visor 300, but instead of having a single button like the visor button 320, it comprises three buttons 720. Each of the buttons is positioned over the respective tab 692 when the visor 700 is mounted onto the helmet shell 602. Pressing down on any of the buttons 720 presses down on a respective button 670 of the actuator panel 668 coupled to a circuit board, which then adjusts a respective setting. For example, one of the buttons may be configured to adjust the shade or darkness of the visor, or there may be one button for adjusting the darkness of a visor port of the visor 700 and another for adjusting the darkness of the remaining or side portions of the visor 700. In one configuration, a middle one of the buttons 720 switches the setting (e.g., darkness) to an active setting, while a top and bottom one of the buttons 720 increase or decrease the active setting. In the illustrated embodiment, the buttons 720 are arranged along an arc on a side portion proximate to a bottom edge of the visor 700. Alternatively, the buttons 720 may be placed on an opposing side of the visor 700, or a front portion of the visor 700. Alternatively, the buttons 720 may also be arranged differently, for example substantially vertically or substantially horizontally.

With specific reference to FIG. 11A, there is shown a cross section of the helmet 600 of FIG. 11 with an auto-darkening welding filter 626 mounted to the helmet shell 602 to at least partially cover the front see-through opening 622. The visor 700 is shaped and dimensioned, when the helmet 600 is configured in the face-protecting configuration (or filter-protecting configuration), to at least partially face an outer surface of the welding filter 626, so as to substantially protect the welding filter 626 from any spatter from the front during a welding process, and because of a tight fit of the visor 700 around edges of the front see-through opening 622 of the protective helmet 600, welding fumes and spatter are prevented from entering a head-receiving cavity of the helmet. The helmet shown in FIG. 11A further comprises a helmet installation-detecting system 628, for determining if a visor mounted onto the helmet is properly installed. The helmet installation-detecting system 628 is substantially described in PCT/US2022/31510, which is incorporated by reference in its entirety.

Figure 11B:
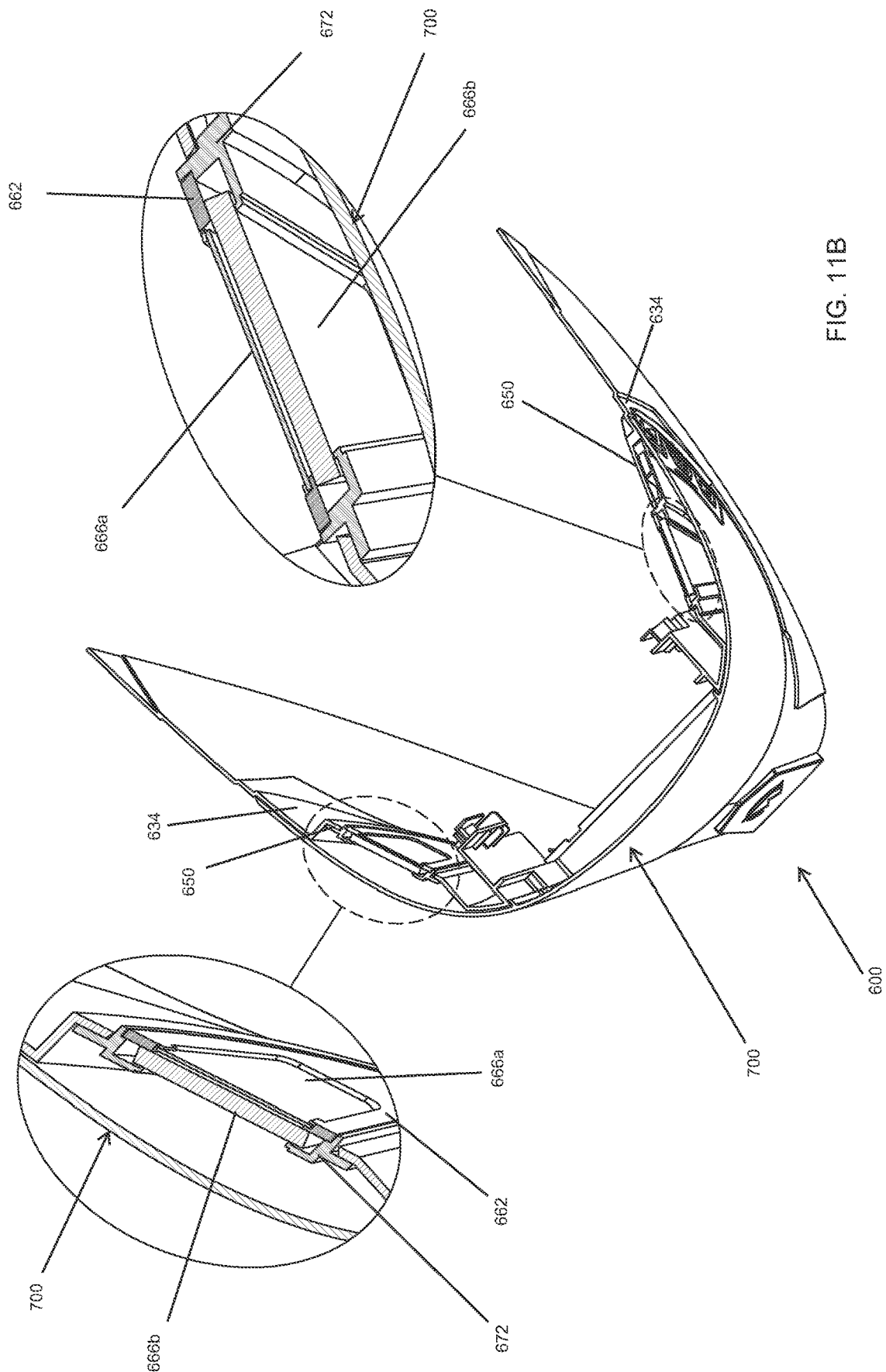
FIG. 11B is a cross-sectional view of the protective helmet taken along cross-section lines 11B-11B of FIG. 11 with partially enlarged views of a button assembly having a side screen between inner and outer frames thereof.

With further reference to FIG. 11B, there is shown a cross section of the helmet 600 of FIG. 11 without the central auto-darkening welding filter but showing the placement of the components of the button assembly 660 on the helmet 600. More specifically, the assembly of the inner frame 662, the side screen 666 and the outer frame 672 is visible with the helmet in the face-protecting configuration. The visor 700 is additionally dimensioned, when the helmet 600 is configured in the face-protecting configuration, to at least partially face the outer surface of the side screen 666, so as to substantially protect the side screen 666 from any spatter from a lateral direction during a welding process, and because of a tight fit of the visor 700 around edges of the side see-through opening 632 of the protective helmet 600, welding fumes and spatter are prevented from entering a head-receiving cavity of the helmet.

Electronic Assembly

In the embodiments shown, the electronic assembly comprises the auto-darkening filter and an electronic control system configured to allow adjustment of one or more controllable settings of the auto-darkening welding filter.

With reference to the helmet 200 of FIGS. 1 and 2, the shell button 260 is operably connected to a mechanical switch mounted on the electronic assembly comprising, for example, the welding filter and the electronic control system. The electronic control system might comprise a circuit board (not shown) mounted to the shell 202, for instance inside the helmet shell. The circuit board controls settings of the auto-darkening filter (not shown). Examples of controllable settings of the auto-darkening filter may be shade, sensitivity, or delay. Although in the illustrated embodiment the electronic control system controls the welding filter, other electronic configurations may be evident or desired. For example, audio output devices such as a speaker or an additional screen for providing a Heads-Up-Display onto the visor may be desired.

For instance, the auto-darkening filter is mounted to the helmet shell and substantially covers the front and/or side see-through openings 222, 232, with the visor 300 providing protection thereto. For instance, the auto-darkening filter is configured to be received in two substantially vertical columns 270 (or substantially parallel filter-mounting members 270) positioned on opposing sides of the front see-through opening 222 and partially bordering the front see-through opening 222. For instance, slots 272 are formed in the substantially parallel filter-mounting members 270 for securely receiving the filter therein. Other means for holding the auto-darkening filter may be evident to the skilled addressee.

In one embodiment, the auto-darkening filter is based on two liquid crystals, with the liquid crystals being electrically switchable between a light state and a dark state. In the dark state, the auto-darkening filter blocks a significant amount of light, such as during welding. In the light state, the user may be able to see in ambient light conditions, for example to survey the work piece prior to welding and without having to take the helmet 200 off. Furthermore, the auto-darkening filter may comprise at least one light sensor coupled to the circuit board and the auto-darkening filter for automatically, in response to light conditions, switching the filter between the dark and light modes. It is envisaged that the auto-darkening filter may be adjustable to several shades in response to light.

Method of Adjusting the Controllable Setting of the Electronic Assembly

It is thus understood that when the visor 300 is positioned (i.e., mounted to) and locked onto the helmet shell 202, the visor button 320 is operably coupled to the depressible side shell button 260. When the user actuates the visor button 320, upon pressure being applied for instance to the actuation face of the depressible member 326, the depressible side shell button 260 is similarly actuated, further actuating the electrical switch of the circuit board of the electronic control system. Although reference has been made to a visor in the above embodiments, any face protecting member or filter-protecting member as evident to the skilled addressee, including visor 700, may be used.

It is thus understood that the face-protecting member 300 is provided with one or more integrated panel tabs that are formed by cutting one or more patterns into the face-protecting member. The integrated panel tab functions as a flexible actuator cooperating with a filter actuator mounted to or formed integral with the helmet shell. Thus, when pressure is applied to the integrated panel tab from the exterior of the protective helmet (by, for example, a finger of a user being applied to the actuation face of the depressible member 326), the applied pressure causes the integrated panel tab to flex and relay at least a portion of the applied pressure to the filter actuator. In other words, a pressure is indirectly applied by the user to the filter actuator via the panel tab of the face-protecting member.

One of the advantages of the helmets 200, 500, 600 relative to other helmets is that the buttons for adjusting settings of the filter are formed integrally with the helmet, so that they don't protrude outwards leading to breakage/accidental use.

Another of the advantages of the presently described helmets 200, 500, 600 is that the addition of a visor comprising a depressible button allows a user to control the settings of the auto-darkening filter on the visor without needing access to the shell. The visor acts as additional protection against dirt and physical damage of the button mounted to or formed integral with the helmet shell since a user does not need to pivot the visor to have access to and actuate the filter actuator mounted to or formed integral with the helmet shell.

One advantage of the helmet 600 is that, in addition to the above and previously described benefits, it allows for multiple settings to be changed discretely from other settings. It also allows for controllable settings to be changed through only a side portion of the helmet 600 due to the side screen 666, so for example the front view and the side view are set at different controllable settings.

Moreover, in the embodiment wherein the depressible visor tab or button cooperates with an actuator—or shell tab—formed integral with the helmet shell, assembly is simplified since there are less steps (as there is no shell button required), while allowing a corresponding reduction in parts which simplifies inventory management.

Several alternative embodiments and examples have been described and illustrated herein. The embodiments of the invention described above are intended to be exemplary only. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind.

The invention claimed is:

1. A protective helmet, comprising:
   a helmet shell at least partially delimiting a head-receiving cavity;
   an electronic assembly having at least one controllable setting; and
   a face-protecting member mountable to the helmet shell to configure the protective helmet into a closed configuration;
   wherein the face-protecting member comprises at least one panel tab selectively depressible to cooperate with an actuator mounted to or formed integral with the helmet shell and operatively coupled to the electronic assembly to adjust said at least one controllable setting upon depression of said at least one panel tab.

2. The protective helmet of claim 1, wherein said at least one panel tab is formed integral with the face-protecting member.

3. The protective helmet of claim 1, further comprising a locking mechanism to selectively configure the face-protecting member in a locked configuration and an unlocked configuration with the helmet shell.

4. The protective helmet of claim 3, wherein the locking mechanism comprises a depressible button configured to be received in a corresponding aperture formed in one of the helmet shell and the face-protecting member.

5. The protective helmet of claim 1, wherein a finger recess is formed in the helmet shell which is configured to be at least partially covered by the face protecting member, the finger recess being shaped and sized to permit removal of the face protecting member via a finger.

6. The protective helmet of claim 1, wherein the actuator comprises a button assembly comprising a button receiving platform mounted to or formed integral with the helmet shell and a depressible button resiliently mounted to the button receiving platform.

7. The protective helmet of claim 1, wherein the electronic assembly comprises a control system having a circuit board configured to allow adjustment of the at least one controllable setting.

8. The protective helmet of claim 1, wherein said at least one controllable setting of the electronic assembly is selected from the group comprised of shade, sensitivity, delay, and work time.

9. A welding helmet, comprising:
   a helmet shell at least partially delimiting a head-receiving cavity, said head-receiving cavity forming a see-through opening in the helmet shell;
   a welding filter mounted to the helmet shell and covering at least partially the see-through opening, said welding filter having at least one controllable setting;
   an electronic control system configured to allow adjustment of said at least one controllable setting of the welding filter;
   a visor mountable to the helmet shell to configure the welding helmet into a welding-protecting configuration, the visor comprising at least one depressible visor button formed integrally with the visor; and
   at least one filter actuator mounted to or formed integral with one of the helmet shell and the welding filter and operatively coupled to the electronic control system;
   wherein the at least one depressible visor button is configured to cooperate with the at least one filter actuator upon being pressed, allowing a user to adjust said at least one controllable setting of the welding filter.

10. The welding helmet of claim 9, wherein the at least one filter actuator comprises a button assembly.

11. The welding helmet of claim 10, wherein the button assembly comprises a button receiving platform mounted to or formed integral with the helmet shell and a depressible button resiliently mounted to the button receiving platform.

12. The welding helmet of claim 9, wherein the at least one filter actuator comprises a shell-mounted button mounted onto the helmet shell and operatively coupled to the at least one visor button.

13. The welding helmet of claim 9, wherein the visor has a visor body, and the at least one depressible visor button extends outwardly from the visor body.

14. The welding helmet of claim 13, wherein the at least one depressible visor button comprises a depressible member and a connecting member forming a flexible junction between the depressible member and the visor body.

15. The welding helmet of claim 14, wherein the depressible member comprises a nipple on an internal surface thereof for actuating the at least one filter actuator.

16. A welding helmet, comprising:
   a helmet shell;
   a visor having at least one integrated depressible visor panel tab formed by cutting a pattern into the visor;
   a button assembly mounted on the helmet shell, the button assembly comprising an actuator panel comprising at least one filter actuator and a button panel having at least one button, the at least one button being operably coupled to the at least one filter actuator; and
   an electronic assembly secured to the helmet shell, the electronic assembly having at least one controllable setting, the electronic assembly being operatively coupled to the at least one filter actuator to control said at least one controllable setting upon actuation thereof;

wherein said at least one integrated depressible visor panel tab at least partially covers said at least one filter actuator and said at least one button to adjust said at least one controllable setting upon depression of said at least one integrated depressible visor panel tab.

17. The welding helmet of claim 16, wherein the button assembly comprises inner and outer frames, the actuator panel being arranged between the inner and outer frames.

18. The welding helmet of claim 17, wherein the at least one button is mounted to or formed integral with the outer frame.

19. The welding helmet of claim 17, wherein the electronic assembly further comprises a side screen comprising an auto-darkening filter mounted between the inner frame and the outer frame.

20. The welding helmet of claim 16, wherein the button panel comprises a plurality of buttons and the at least one integrated depressible visor panel tab comprises a corresponding number of depressible tabs operatively coupled to the plurality of buttons.

* * * * *